(12) United States Patent
Ohta et al.

(10) Patent No.: US 7,368,115 B2
(45) Date of Patent: *May 6, 2008

(54) METHOD OF ENHANCING NEURAL STEM CELL PROLIFERATION, DIFFERENTIATION, AND SURVIVAL USING PITUITARY ADENYLATE CYCLASE ACTIVATING POLYPEPTIDE (PACAP)

(75) Inventors: Shigeki Ohta, Tokyo (JP); Samuel Weiss, Calgary (CA)

(73) Assignee: Stem Cell Therapeutics Inc., Calgary, Alberta ( * ) Notice: Subject to any disclaimer, the term of this patent is extended or adjusted under 35 U.S.C. 154(b) by 428 days.

This patent is subject to a terminal disclaimer.

(21) Appl. No.: 10/630,967

(22) Filed: Jul. 31, 2003

(65) Prior Publication Data

US 2004/0092448 A1 May 13, 2004

Related U.S. Application Data

(60) Provisional application No. 60/399,390, filed on Jul. 31, 2002.

(51) Int. Cl.
 *A61K 36/00* (2006.01)
 *A61K 36/18* (2006.01)
 *A62K 36/15* (2006.01)

(52) U.S. Cl. .................. 424/198.1; 435/365; 435/368; 435/377; 514/12; 530/399

(58) Field of Classification Search ...................... None
See application file for complete search history.

(56) References Cited

U.S. PATENT DOCUMENTS

| | | |
|---|---|---|
| 4,767,628 A | 8/1988 | Hutchinson |
| 5,023,252 A | 6/1991 | Hseih |
| 5,128,242 A | 7/1992 | Arimura et al. |
| 5,198,542 A | 3/1993 | Onda et al. |
| 5,208,320 A | 5/1993 | Kitada et al. |
| 5,231,178 A | 7/1993 | Holtz et al. |
| 5,268,164 A | 12/1993 | Kozarich |
| 5,326,860 A | 7/1994 | Onda et al. |
| 5,473,054 A | 12/1995 | Jameson |
| 5,506,107 A | 4/1996 | Cunningham |
| 5,506,206 A | 4/1996 | Kozarich |
| 5,521,069 A | 5/1996 | Onda et al. |
| 5,527,527 A | 6/1996 | Friden |
| 5,547,935 A | 8/1996 | Mullenbach et al. |
| 5,559,143 A | 9/1996 | McDonald |
| 5,614,184 A | 3/1997 | Sytkowski et al. |
| 5,623,050 A | 4/1997 | Kitada et al. |
| 5,686,416 A | 11/1997 | Kozarich |
| 5,723,115 A | 3/1998 | Serrero |
| 5,750,376 A | 5/1998 | Weiss et al. |
| 5,753,506 A | 5/1998 | Johe |
| 5,773,569 A | 6/1998 | Wrighton et al. |
| 5,801,147 A | 9/1998 | Kitada et al. |
| 5,833,988 A | 11/1998 | Friden |
| 5,837,460 A | 11/1998 | Von Feldt et al. |
| 5,851,832 A | 12/1998 | Weiss et al. |
| 5,877,169 A | 3/1999 | Simpkins |
| 5,885,574 A | 3/1999 | Elliott |
| 5,955,346 A | 9/1999 | Wells et al. |
| 5,977,307 A | 11/1999 | Friden et al. |
| 5,980,885 A | 11/1999 | Weiss et al. |
| 6,015,555 A | 1/2000 | Friden |
| 6,017,533 A | 1/2000 | Moro et al. |
| 6,048,971 A | 4/2000 | Sytkowski et al. |
| 6,165,783 A | 12/2000 | Weiss et al. |
| 6,191,106 B1 | 2/2001 | Mullenbach et al. |
| 6,239,105 B1 | 5/2001 | Brewitt |
| 6,242,563 B1 | 6/2001 | Dong |
| 6,294,346 B1 | 9/2001 | Weiss et al. |
| 6,329,508 B1 | 12/2001 | Friden |
| 6,333,031 B1 | 12/2001 | Olsson et al. |
| 6,399,316 B1 | 6/2002 | Onda et al. |
| 6,413,952 B1 | 7/2002 | Luengo et al. |
| 6,429,186 B1 | 8/2002 | Fuh et al. |
| 6,551,618 B2 | 4/2003 | Baird et al. |
| 6,680,295 B1 * | 1/2004 | Arimura ...................... 514/12 |
| 6,797,264 B1 | 9/2004 | Eriksson |
| 7,048,934 B2 * | 5/2006 | Thompson et al. ...... 424/198.1 |
| 2002/0098178 A1 | 7/2002 | Brand |
| 2003/0049838 A1 | 3/2003 | Thompson et al. |
| 2003/0054551 A1 | 3/2003 | Shingo et al. |
| 2003/0054998 A1 | 3/2003 | Shingo et al. |
| 2004/0038888 A1 * | 2/2004 | Mercer et al. ................ 514/12 |
| 2006/0121007 A1 | 6/2006 | Thompson et al. |
| 2006/0148084 A1 | 7/2006 | Shingo et al. |
| 2007/0098698 A1 | 5/2007 | Gregg et al. |
| 2007/0179092 A1 | 8/2007 | Ohta et al. |

FOREIGN PATENT DOCUMENTS

EP 0 456 279 A3 1/1992

(Continued)

OTHER PUBLICATIONS

Whittemore et al., Exp Cell Res. Oct. 10, 1999;252(1):75-95.*

(Continued)

*Primary Examiner*—Manjunath Rao
*Assistant Examiner*—Daniel C Gamett
(74) *Attorney, Agent, or Firm*—Fish & Richardson P.C.

(57) ABSTRACT

The present invention relates to a method of increasing the number and/or differentiation of neural stem cells and/or neural stem cell progeny using pituitary adenylate cyclase-activating polypetide (PACAP). In a preferred embodiment, additional growth factors are also utilized. The present invention can be practiced in vivo and in vitro, rendering it useful for the treatment of neurodegenerative disease and other neural trauma.

42 Claims, 4 Drawing Sheets

FOREIGN PATENT DOCUMENTS

| | | |
|---|---|---|
| EP | 0 467 279 A3 | 1/1992 |
| WO | WO 90 05185 | 5/1990 |
| WO | WO93/01275 | 1/1993 |
| WO | WO 96 40231 | 1/1993 |
| WO | WO 00 13650 | 4/1994 |
| WO | WO94/10292 | 5/1994 |
| WO | WO 97 48729 | 5/1994 |
| WO | WO 99 15191 | 3/1996 |
| WO | WO9609318 A * | 3/1996 |
| WO | WO 99 21966 | 5/1999 |
| WO | WO 99 51272 | 10/1999 |
| WO | WO 00 05260 | 2/2000 |
| WO | WO 00 30675 | 6/2000 |
| WO | WO 200030675 A2 | 6/2000 |
| WO | WO 03/018782 | 3/2003 |
| WO | WO 03 24472 | 3/2003 |
| WO | WO 03/040310 | 5/2003 |
| WO | WO 03 92716 | 11/2003 |

OTHER PUBLICATIONS

Schlessinger et al., Molecular Cell. Sep. 2000;6(3):743-50.*
Hirose, M. et al., "Gene expression of PACAP and its receptors in the ES cell-derived neuronal stem cells." Japanese Journal of Pharmacology, The Japanese Pharmacological Society, Kyoto, JP, vol. 88, No. suppl. 1, p. 143.
Lelievre, V. et al., "Fibroblast growth factor-2 converts PACAP growth action on embryonic hindbrain precursors from stimulation to inhibition." Journal of Neuroscience Research, vol. 67, No. 5, Mar. 1, 2002, pp. 566-573.
Lelievre, V. et al., "Cross-talk between PACAP and sonic hedgehog (SHH) pathways in neural stem cells, cerebellar granular progenitor cells and oligodendrocyte progenitors to control cell fate and proliferation." Regulatory Peptides, vol. 115, No. 1, 2003, p. 50.
Lelievre, V. et al., "Interactive of PACAP with sonic Hedgehog on neural stem cell and oligodendrocyte progenitor proliferation." Journal of Neurochemistry, vol. 85, No. Supplement 1, May 20, 2003, p. 66.
Ohta et al., "Pituitary adenylate cyclase-activating polypeptide (PACAP) regulates forebrain neural stem cell fate in vitro and in vivo," Society for Neuroscience Abstract Viewer and Itinerary Planner, vol. 2002, page abstract No. 329.13, 2002.
Pesce, Mauricio et al., "Pituitary adenylate cyclass-activating polypeptide (PACAP) stimulates adenylate cyclase and promotes proliferation of mouse primordial germ cells." Development (Cambridge), vol. 122, No. 1, 1996, pp. 215-221.
Rostene, W. et al., "VIP and PAGAP via G-Protien coupled receptors are potent inducers of mouse embryonic stem cell neuronal differentiation." Regulatory Peptides, vol. 115, No. 1, 2003, p. 55.
Vaudry, David et al., "Neurotrophic activity of pituitary adenylate cyclase-activating polypeptide on rate cerebellar cortex during development." Proceeding of the National Academy of Sciences of the United States, vol. 96, No. 16, Aug. 3, 1999, pp. 9415-9420.
A. Arimura, "Pituitary Adenylate Cyclase Activating Polypeptide (PACAP):Discovery and Current Status of Research", Regulatory Peptides, 37:287-303 (1992). Elsevier Science Publishers.
A. Arimura et al., "Perspectives on Pituitary Adenylate Cyclase Activating Polypeptide (PACAP) in the Neuroendocrine, Endocrine, and Nervous Systems", Jap. J. Physiol. 48:301-331 (1998). Center for Academic Publications, Japan.
A. Arimura et al., "Tissue Distribution of PACAP as Determined by RIA: Highly Abundant in the Rat Brain Testes", Endocrinol. 129:2787-2789 (1991). Williams & Wilkins.
A. Arimura et al., "PACAP Functions as a Neurotrophic Factor", Ann. N.Y. Acad. Sci. 739:228-243 (1994), New York Academy of Science, New York.
W.A. Banks et al., "Passage of Pituitary Adenylate Cyclase Activating Polypeptide 1-27 and Pituitary Adenylate Cyclase . . . ", J. Pharmacol. Exp. Ther. 267(2):690-6 (1993). William & Wilkins.
S.A. Bayer, "Neuron Production in the Hippocampus and Olfactory Bulb of the Adult Rat Brain: Addition or Replacement?", N.Y. Acad. Sci. 457:163-173 (1985). New York Academy of Sciences, New York.
S. Bernichtein et al., "S179D-human PRL, a Pseudeophosphorylated Human PRL Analog, is an Agonist and not an Antagonist", Endocrinology 142(9):3950-3963 (2001). The Endocrine Society.
R.G. Carey et al., "Pituitary Adenylate Cyclase Activating Polypeptide Antimitogenic Signaling in Cerebral Cortical Progenitors is Regulated by p57Kip2-dependent CDK2 activity," J. Neurosci. 22(5):1583-91 (2002). Society for Neuroscience.
J. Christophe, "Type I Receptors for PACAP (a neuropeptide even more important than VIP?)" Biochim. Biophys. Acta 1154:183-99 (1993). Elsevier Science Publishers.
C.G. Craig et al., "In vivio Growth Factor Expansion of Endogenous Subependymal Neural Precursor Cell Populations in Adult Mouse Brain," J. Neurosci. 16(8):2649-58 (1996) Society for Neuroscience.
C.R. Freed et al., "Survival of Implanted Fetal Dopamine Cells and Neurologic Improvement 12 to 46 Months After Transplantation for Parkinson's Disease", N. Engl. J. Med. 327:1549-1555 (1992).
D.E. Hansel et al., "Regulation of Olfactory Neurogenesis by Amidated Neuropeptides,", J. Neurosci. Res. 66:1-7 (2001). Wiley-Liss.
H. Hashimoto et al., "Altered Psychomotor Behaviors in Mice Lacking Pituitary Adenylate Cyclase-Activating Polypeptide (PACAP)", PNAS 98:(23)13355-13360 (2001).
H. Hashimoto et al., "Molecular Cloning and Tissue Distribution of a Receptor for Pituitary Adenylate Cyclase Activating Polypeptide", Neuron 11:333-342 (1993). Cell Press.
M.S. Kaplan, "Neurogenesis in the 3-month Old Rat Visual Cortex," J. Comp. Neurol. 195:323-338 (1981). Alan R. Liss.
C. Kimura et al., "A Novel Peptide Which Stimulates Adenylate Cyclase: Molecular Cloning and Characterization of the Ovine and Human cDNAs," Biochem. Biophys. Res. Comm. 166:81-89 (1990). Academic Press.
D. Van Der Kooy and S. Weiss, "Why Stem Cells?", Science 287:1439-41 (2000).
D. Lindholm et al., "Developmental Regulation of Pituitary Adenylate Cyclase Activating Polypeptide (PACAP) and its Receptor 1 in Rat Brain: Function of PACAP as a Neurotrophic Factor," Ann. N.Y. Acad. Sci. 865:189-96 (1998). New York Acad. Sciences, New York.
N. Lu et al., "Pituitary Adenylate Cyclase-Activating Polypeptide is an Autocrine Inhibitor of Mitosis in cultured Cortical Precursor Cells," Proc. Natl. Acad. Sci. USA 94:3357-3362 (1997). The Natl. Acad. of Sciences of the USA.
A. Miyata et al., "Isolation of a Novel 3B Residue-Hypothalamic Polypeptide which Stimulates Adenylate Cyclase in PituitaryCells," Biochem. Bophys. Res. Comm. 164:567-574 (1989). Academic Press.
A. Nicot et al., "Regulation of Neuroblast Mitosis is Determined by PACAP Receptor Isoform Expression", PNAS 98:(8)4758-4763 (2001).
C. Otto et al., "Altered Emotional Behavior in PACAP-type-I-receptor-deficient Mice," Brain Res. Mol. Brain Res. 91(1-2):78-84 (2001). Elsevier Science.
M.J. Perlow et al., "Brain Grafts Reduce Motor Abnormalities Produced by Destruction of Nigrostriatal Dopamine System," Science 204:643-647 (1979). Amer. Acad. for the Advancement of Science.
C.S. Potten and Loeffler, "Stem Cells: Attributes, Cycles, Spirals, Pitfalls and Uncertainties. Lessons for and from the Crypt," Development 110:1001-1020 (1990). Company of Biologists, Ltd.
P. Rakic, "Limits of Neurogenesis in Primates," Science 227:1054-1056 (1985).
S.R. Rawlings, "At the Cutting Edge PACAP, PACAP Receptors, and Intracellular Signalling", Mol. and Cellular Endocrinol. 191:C5-C9 (1994). Elsevier Science Ireland Ltd.
B.A. Reynolds and S. Weiss, "Generation of Neurons and Astrocytes from Isolated Cells of the Adult Mammalian Central Nervous Systems," Science 255:1701-1710 (1992).

R. Rietze et al., "Mitotically Active Cells that Generate Neurons and Astrocytes are Present in Multiple Regions of the Adult Mouse Hippocampus," J. Comp. Neurol. 424(3):397-408 (2000). Wiley-Liss.

T. Shingo et al., "Erythropoietin Regulates the *in vitro* and *in vivo* Production of Neuronal Progenitors by Mammalian Forebrain Neural Stem Cells," J. Neurosci. 21(24):9733-9743 (2001). Society for Neuroscience.

D.D. Spencer et al., "Unilateral Transplantation of Human Fetal Mesencephalic Tissue into the Caudate Nucleus of Patients with Parkinson's Disease," New Engl. J. Med. 327:1541-1548 (1992). Massachusetts Medical Society.

D. Vaudry et al., "Pituitary Adenylate Cyclase-Activating Polypeptide and Its Receptors from Structure to Functions," Pharmacol. Rev. 52:269-324 (2000). The Amer. Soc. for Pharmacol. & Exp. Ther.

J.A. Waschek, "VIP and PACAP Receptor-mediated Actions on Cell Proliferation and Survival," Ann. N.Y. Acad. Sci. 805:290-300 (1996). New York Academy of Sciences, New York.

H. Widner et al., "Bilateral fetal Mesencephalic Grafting into Two Patients with Parkinsonism Induced by 1-methyl-4-phenyl-1,2,3,6-tetrahydropyridine (MPTP)," N. Engl. J. Med. 327:1556-1563 (1992). Massachusetts Medical Society.

A. Yuhara et al., "PACAP has a Neurotrophic Effect on Cultured Basal Forebrain Cholinergic Neurons from Adult Rats," Brain Res. Dev. Brain Res. 131(1):41-5 (2001). Elsevier Science.

Aberg, M.A.I. et al. "Peripheral Infusion of IGF-I Selectively Induces Neurogenesis in the Adult Rat Hippocampus." J of Neuro., vol. 20, No. 8, pp. 2896-2903 (Apr. 15, 2000).

Abramsky, O. et al. "Suppressive Effect of Pregnancy on Ms and EAE" Prog. Clin. Biol. Res., pp. 399-406 (1984).

Allen, J.S. et al. "Sexual dimorphism and asymmetries in the gray-white composition of the human cerebrum" NeuroImage, vol. 18, pp. 880-894 (2003).

Anderson, M.F. et al. "Insulin-like growth factor-I and neurogenesis in the adult mammalian brain." Brain Res Dev Brain Res., vol. 134, Nos. 1-2, pp. 115-22 (Mar. 31, 2002).

Armstrong, R.C. et al. "Absence of fibroblast growth factor 2 promotes oligodendroglial repopulation of demyelinated white matter" J Neurosci., vol. 22, No. 19, pp. 8574-8585 (2002).

Arnett, H.A. et al. "TNF-α promotes proliferation of oligodendrocyte progenitors and remyelination" Nature, vol. 4, pp. 1116-22 (2001).

Arsenijevic & Weiss "Insulin-like Growth Factor-I (IGF-I) Recruits a Distinct Population of Embryonic Neural Stem Cells, " Molecular Biology of the Cell, vol. 7 (Supp), p. 1842, (Dec. 1996).

Aston, C., et al. "Transcriptional profiling reveals evidence for signaling and oligodendroglial abnormalities in the temporal cortex from patients with major depressive disorder" Mol Psychiatry vol. 10, pp. 309-322 (2005).

Bambakidis, N. C. and Miller, R. H. "Transplantation of oligodendrocyte precursors and sonic hedgehog results in improved function and white matter sparing in the spinal cords of adult rats after confusion" J Spine, vol. 4, p. 16-26 (2004).

Bartzokis, G., et al. "Heterogeneous age-related breakdown of white matter structural integrity: implications for cortical "disconnection" in aging and Alzheimer's disease" Neurobiol Aging, vol. 25, pp. 843-851 (2004).

Bebo, Jr., B. F. and Dveksler, G. S. "Evidence that pregnancy specific glycoproteins regulate T-Cell function and inflammatory autoimmune disease during pregnancy" Curr. Drug Targets Inflamm. & Allergy. vol. 4, pp. 231-237 (2005).

Bebo, Jr., B.F. et al. "Low-dose estrogen therapy ameliorates experimental autoimmune encephalomyelitis in two different inbred mouse strains" J. Immunol., vol. 166, pp. 2080-2089 (2001).

Bruck, W. and Stadelmann, C. "The spectrum of multiple sclerosis: new lessons from pathology" Curr Opin Neurol, vol. 18, pp. 221-224 (2005).

Buckner, R.L. "Memory and executive function in aging and AD: multiple factors that cause decline and reserve factors that compensate" Neuron, vol. 44, pp. 195-208 (2004).

Camarillo, I. G. et al. "Prolactin receptor expression in the epithelia and stroma of the rat mammary gland" J Endocrinol, vol. 171, pp. 85-95 (2001).

Cao, Q. et al. "Functional recovery in traumatic spinal cord injury after transplantation of multineurotrophin-expressing glial-restricted precursor cells" J Neurosci, vol. 25, No. 30, pp. 6947-6957 (2005).

Cerghet, M. et al. "Proliferation and death of oligodendrocytes and myelin proteins are differentially regulated in male and female rodents" J Neurosci, vol. 26, No. 5, pp. 1439-1447 (2006).

Cerani, A. et al. "Effects of Epoetin on the Central Nervous System" Seminars in Oncology, vol. 28, No. 2. Suppl 8, pp. 66-70 (Apr. 2001).

Chikanza, I. C. "Prolactin and neuroimmunomodulation: in vitro and in vivo observations" Ann. N. Y. Acad. Sci., vol. 876, pp. 119-130 (1999).

Chojnacki, A. and Weiss, S. "Isolation of a novel platelet-derived growth factor-responsive precursor from the embryonic ventral forebrain" J. Neurosci., vol. 24, No. 48, pp. 10888-10899 (2004).

Confavreux, C. et al. Rate of pregnancy-related relapse in multiple sclerosis. N Engl J Med., vol. 339, No. 5, pp. 285-91 (1998).

Cunningham, B. C., et al. "High-resolution epitope mapping of hGH-receptor interactions by alanine-scanning mutagenesis", Sci., vol. 244, p. 4908 (1989).

Cunningham, B.C. et al. "Receptor and antibody epitopes in human growth hormone identified by homolog-scanning mutagenesis" Sci., vol. 243, No. 4896, pp. 1330-1336 (1989).

Dawson, M.R.L. et al. "NG2-expressing glial progenitor cells" an abundant and widespread population of cycling cells in the adult rat CNS Mol Cell Neurosci, vol. 24, pp. 476-488 (2003).

Devito, W.J., et al. "Prolactin induced expression of interleukin-1 alpha, tumor necrosis factoralpha, and transforming growth factor-alpha in cultured astrocytes", J. Cell Biochem. 57:290-298 (1995).

Dicco-Bloom., et al. "The PACAP Ligand/Receptor System Regulates Cerebral Cortical Neurogenesis", Annals of the N.Y. Aca. of Sci. pp. 274-289 (1998).

Dong, W. K. and Greenough W. T. "Plasticity of nonneuronal brain tissue: roles in developmental disorders" Ment Retard Dev Disabil Res. Rev., vol. 10, pp. 85-90 (2004).

Draca, S. and Levic, X. "The possible role of prolactin in the immunopathogenesis of multiple sclerosis" Med. Hypotheses, vol. 47, pp. 89-92 (1996).

Dubey, A.K. et al. "Differential Penetration of Three Anterior Pituitary Peptide Hormones into the cerebrospinal fluid of rhesus monkeys" Life Sci., vol. 32, Issue 16, pp. 1857-1863 (Apr. 18, 1983) abstract.

Faulkner, J. and Keirstead, H. S. "Human embryonic stem cell-derived oligodendrocyte progenitors for the treatment of spinal cord injury" Transpl. Immunol., vol. 15, pp. 131-142 (2005).

Fernandez-Pol, J.A. "Epidermal growth factor receptor of A431 cells. Characterization of a monoclonal anti-receptor antibody non-competitive agonist of epidermal growth factor action" J. Biol. Chem., vol. 260, Issue 8, pp. 5003-5011 (1985).

Ferro, J. M. and Madureira, S. "Age-related white matter changes and cognitive impairment" J Neurol Sci., vols. 203-204, pp. 221-225 (2002).

Fields, R.D. "Myelination: an overlooked mechanism of synaptic plasticity?" Neuroscientist, vol. 11, pp. 528-531 (2005).

Fleming, A. S. and Walsh, C. "Neuropsychology of maternal behavior in the rat: c-fos expression during mother-litter interactions" Psychoneuroendocrinology vol. 19, Nos. 5-7, pp. 429-443 (1994).

Freeman, M.E., et al., "Prolactin: structure, function and regulation of secretion", Physiol. Rev. 80: 1523-1631 (2000).

Gage, F.H. et al. "Isolation, characterization, and use of stem cells from the CNS." Annu Rev Neurosci, vol. 18, pp. 159-92 (1995).

Gage, F.H. et al. "Survival and differentiation of adult neuronal progenitor cells transplanted to the adult brain." Proc Natl Acad Sci., vol. 92, pp. 11879-83 (Dec. 5, 1995).

Gage, F.H. "Mammalian neural stem cells" Sci., vol. 287, pp. 1433-8 (2000).

Gatewood, J.D. et al., "Motherhood mitigates aging-related decrements in learning and memory and positively affects brain aging in the rat" Brain Res Bull, vol. 66, pp. 91-98 (2005).

Gensert, J. M. and Goldman J. E., "In vivo characterization of endogenous proliferating cells in adult rat subcortical white matter" GLIA, vol. 17, pp. 39-51 (1996).

Gensert, J. M. and Goldman, J. E. "Endogenous progenitors remyelinate demyelinated axons in the adult CNS" Neuron, vol. 19, pp. 197-203 (1997).

Goeddeli, D.V., et al. Direct expression in Escherichia coli of a DNA sequence coding for human growth hormone. Nature, vol. 281, No. 5732, pp. 544-548 (1979).

Gray, G.L., et al. Periplasmic production of correctly processed human growth hormone in Escherichia coli: natural and bacterial signal sequences are interchangeable. Gene, vol. 39, Nos. 2-3, pp. 247-254 (1985).

Goffin et al. "Sequence-Function Relationships within the Expanding Family of Prolactin, Growth Hormone, Placental Lactogen, and Related Proteins in Mammals" Endocrine Reviews, vol. 17, pp. 385-410 (Jan. 2007).

Gur, R. C. et al. "Sex differences in brain gray and white matter in healthy young adults: correlations with cognitive performance" J Neurosci, vol. 19, No. 10, pp. 4065-4072 (1999).

Hack, M. A. et al. "Neuronal fate determinants of adult olfactory bulb neurogenesis" Nat Neurosci, vol. 8, No. 7, pp. 865-872 (2005).

Haier, R.J. et al. "The neuroanatomy of general intelligence: sex matters" Neuroimage vol. 25, pp. 320-327 (2005).

Inzitari, D. "Leukoaraiosis: An independent risk factor for stroke?" Stroke, vol. 34, pp. 2067-2071 (2003).

Ito, A. et al. "Estrogen treatment down-regulates TNF-α production and reduces the severity of experimental autoimmune encephalomyelitis in cytokine knockout mice" J Immunol, vol. 167, pp. 542-552 (2001).

Johnson, D.L., et al. "Erythropoietin mimetic peptides and the future" Nephrol. Dial. Transplant, vol. 15, Issue 9, pp. 1274-1277 (2000).

Jokinen, H. et al. "Medial temporal lobe atrophy and memory deficits in elderly stroke patients" Eur J Neurol 11:825-832 (2004).

Kandel et al. "Principles of Neural" Sci. p. 981-1991.

Karimi-Abdolrezaee, S. et al., "Delayed transplantation of adult neural precursor cells promotes remyelination and functional neurological recovery after spinal cord injury" J Neurosci., vol. 26, No. 13, pp. 3377-3389 (2006).

Kaushansky, K. "Hematopoietic growth factor mirnetics" Ann. N.Y. Acad. Sci. 938: 131-138 (2001).

Keirstead, H.S. et al. "Human embryonic stem cell-derived oligodendrocyte progenitor cell transplants remyelinate and restore locomotion after spinal cord injury" J Neurosci., vol. 25, No. 19, pp. 4694-4075 (2005).

Kieseier, B.C. et al. "Multiple sclerosis-novel insights and new therapeutic strategies" Curr Opin Neurol., vol. 18, pp. 211-220 (2005).

Kim, J. H. and Juraska, J. M. "Sex differences in the development of axon number in the splenium of the rat corpus callosum from postnatal day 15 through 60" Brain Res. Dev. Brain Res., vol. 102, p. 77-85 (1997).

Kim, S. et al. "Estriol ameliorates autoimmune demyelinating disease: implications for multiple sclerosis" Neurology, vol. 52, pp. 1230-1238 (1999).

Kinsley, C. H. et al. "Motherhood improves learning and memory" Nature, vol. 402, p. 137 (1999).

Kolb, B. et al. "Nerve growth factor treatment prevents dendritic atrophy and promotes recovery of function after cortical injury" Neuros., vol. 76, Issue 4, pp. 1139-1151 (1997).

Konishi Y., et al. "Trophic effect in erythropoietin and or hematopoietic factors on central cholinergic neurons in vitro and in vivo" Brain Res. vol. 609, pp. 29-35 (1993).

Kovacs, T. et al. "olfactory Bulb in Multiple System Atrophy", Movement Disorder, vol. 18, No. 8, pp. 938-942 (2003).

Lambert, K. G. et al. "Pup exposure differentially enhances foraging ability in primiparous and nulliparous rats" Physiol. Behav., vol. 84, pp. 799-806 (2005).

Learish, R.D. et al. "Intraventricular transplantation of oligodendrocyte progenitors into a fetal myelin mutant results in widespread formation of myelin" Ann Neurol, vol. 46, pp. 716-722 (1999).

Lee, K. H. et al., "Effects of glial transplantation on functional recovery following acute spinal cord injury" J. Neurotrauma 22(5):575-589 (2005).

Lee, M. et al., "Pituitary Adenylyl Cyclase-Activating Polypeptide Stimulates DNA synthesis but Delays Maturation of Oligodendrocyte Progenitors", Journal of Neuroscience, vol. 21, No. 11, pp. 3849-3859 (2001).

Levine, J.M. et al. "The oligodendrocyte precursor cell in health and disease" Trends Neurosci., vol. 24, No. 1, pp. 39-47 (2001).

Levison, S.W. et al. "Cycling cells in the adult rat neocortex preferentially generate oligodendroglia" J Neurosci Res., vol. 57, pp. 435-466 (1999).

Lim, D.A., "Noggin antagonizes BMP signaling to create a niche for adult neurogenesis", Neuron, vol. 28, pp. 713-726 (2000).

Lindholm et al. "Developmental Regulation of Pituitary Adenylate Cyclase Activating Polypeptide (PACAP) and its Receptor 1 in Rat Brain: Function of PACAP as a Neurotrophic Factor," Ann. N.Y. Acad. Sci., vol. 865, pp. 189-96 (1998).

Livnah, O., et al. "Functional mimicry of a protein hormone by a peptide agonist: the EPO receptor complex at 2.8 A" Sci. vol. 273, Issue 5274, pp. 464-471 (1996).

Lledo, P. M. et al. "Adult neurogenesis and functional plasticity in neuronal circuits" Nat Rev Neurosci, vol. 7, pp. 179-193 (2006).

Love, G. et al. "Maternal experience produces long-lasting behavioral modification in the rat" Behav Neurosci., vol. 119, No. 4, pp. 1084-1096 (2005).

Lowman, H.B. et al. "Mutational analysis and protein engineering of receptor-binding determinants in human placental lactogen" J. Biol. Chemistry, vol. 266(17), pp. 10982-10988 (1991).

Lubetzki, C. et al. "Promoting repair in multiple sclerosis: problems and prospects" Curr Opin Neurol., vol. 18, pp. 237-244 (2005).

Lyoo, I.K. et al. "White matter hyperintensities on magnetic resonance imaging of the brain in children with psychiatric disorders" Compr Psychiatry, vol. 43, No. 5, pp. 361-368 (2002).

Mack, C. M. et al. "Sex differences in the distribution of axon types within the genu of the rat corpus callosum" Brain Res, vol. 697, pp. 152-156.

Menn, B. et al. "Origin of oligodendrocytes in the subventricular zone of the adult brain" J Neurosci., vol. 26, No. 30, pp. 7907-7918 (2006).

Mode, A., et al. "The human growth hormone (hGH) antagonist G120RhGH does not antagonize GH in the Rat, but has paradoxical agonist activity, probably via the prolactin receptor" Endocrinology, vol. 137, Issue 2, pp. 447-454 (1996).

Moderscheim et al. "Prolactin is Involved in Glial Responses Following a Focal Injury to the Juvenile Rat Brain" Neuroscience, vol. 145, pp. 963-973 (2007).

Moore, P.B. et al. "Cerebral white matter lesions in biopolar affective disorder: relationship to outcome" Br J Psychiatry, vol. 178, pp. 172-176 (2001).

Mori, E. "Impact of subcortical ischemic lesions on behavior and cognition" Ann. N. Y. Acad Sci., vol. 977, p. 141-148 (2002).

Nait-Oumesmar, B. et al. "Progenitor cells of the adult mouse subventricular zone proliferate, migrate and differentiate into oligodendrocytes after demyelination" Eur J Neurosci., vol. 11, pp. 4357-4366 (1999).

Neumann, I. D. "Alterations into behavioral and neuroendocrine stress coping strategies in pregnant, parturient and lactating rats" Prog. Brain Res., vol. 133, pp. 143-152 (2001).

Nunez, J. L. et al. "Myelination in the splenium of the corpus callosum in adult male and female rats" Dev Brain Res., vol. 120, pp. 87-90 (2000).

Nyberg, F. "Aging effects on growth hormone receptor binding in the brain", Exp. Gerontol, vol. 32, Nos. 4-5, pp. 521-528 (1997).

Nyberg, F. "Growth hormone in the brain: characteristics of specific brain targets for the hormone and their functional significance", Front Neuroendocrinol., vol. 21, pp. 330-348 (2000).

Ormandy, C. J. et al. "Null mutation of the prolactin receptor gene produces multiple reproductive defects in the mouse" Genes Dev., vol. 11, pp. 167-178 (1997).

Peters, A. and Sethares C. "Oligodendrocytes, their progenitors and other neuroglial cells in the aging primate cerebral cortex" Cereb Cortex, vol. 14, pp. 995-1007 (2004).

Peters, A. et al., "Effects of aging on the neuroglial cells and pericytes within area 17 of the rhesus monkey cerebral cortex" Anat rec, vol. 229, pp. 384-398 (1991).

Peters, A. J. "The effects of normal aging on myelin and nerve fibers: a review" J Neurocytol, vol. 31, pp. 581-593 (2002).

Phelps, C.J, et al., "Stimulatory effect on human, but not bovie, growth hormone expression on numbers of tuberoinfundibular dopaminergic neurons in transgenic mice", Endocrinology, vol. 138, No. 7, pp. 2849-2855 (1997).

Phelps, C.J. et al., "Pituitary hormones as neurotrophic signals: Update on hypothalamic differentiation in genetic models of altered feedback", Proc. of the Soc. for Exp. Biology and Medicine, vol. 222, No. 1, pp. 39-58 (1999).

Picard-Riera, N. et al., "Experimental autoimmune encephalomyelitis mobilizes neural progenitors from the subventricular zone to undergo oligodendrogenesis in adult mice" PNAS 99(20):13211-13216 (2002).

Polito, A. and Reynolds R. "NG2 expressing cells as oligodendrocyte progenitors in the normal and demyelinated adult central nervous system" Anat. 207:707-716 (2005).

Rochefort, C., et al. "Enriched odor exposure increases the number of newborn neurons in the adult olfactory bulb and improves odor memory" J Neurosci., vol. 22, No. 7, pp. 2679-2689 (2002).

Scheepens, A. et al. "Growth Hormone as a Neuronal Rescue Factor During Recovery from CNS Injury." Neuroscience, vol. 104, No. 3, pp. 677-687 (Jun. 14, 2001).

Schradin, C. and Anzenberger G. "Prolactin, the Hormone of Paternity" News Physiol Sci., vol. 14, pp. 223-231 (1999).

Scolding, N. J. and Franklin, R. J. M. "Remyelination in demyelinating disease" Baillieres Clin Neurol., vol. 6(3), pp. 525-548 (1997).

Shimazaki, T. et al. "The ciliary neurotrophic factodleukemia inhibitory factor/gp130 receptor complex operates in the maintenance of mammalian forebrain neural stem cells" J. Neurosci., vol. 21, No. 19, pp. 7642-7653 (2001).

Shingo, T. et al. "Pregnancy-stimulated neurogenesis in the adult female forebrain mediated by prolactin" Sci., vol. 299, pp. 117-120 (2003).

Shingo, T. Shingo et al., Supporting Online Material pp. 1-10.

Shioda, J. et al. "Pleiotropic functions of PACAP in the CNS. Neuroprotection and neurodevelopment" Ann. NY Acad. Sci., vol. 1070, pp. 550-60 (2006).

Sicotte, N. L. et al. "Treatment of multiple sclerosis with the pregnancy hormone estriol" Ann Neurol., vol. 52, pp. 421-428 (2002).

Silverstone, T. et al. "Deep white matter hyperintensities in patients with bipolar depression, unipolar depression and age-matched control subjects" Bipolar Disord, vol. 5, pp. 53-57 (2003).

Sirevaag, A. M. and Greenough, W. T. "Differential rearing effects on rat visual cortex synapses. III. Neuronal and glial nuclei, boutons, dendrites and capillaries" Brain Res., vol. 424, pp. 320-332 (1987).

Sorokan, S.T. et al., "Erythropoietin mediates increased neurogenesis by embryonic CNS stem cells following a modest hypoxic insult", Society for Neuroscience Abstracts, 23(1/2):320 (1997).

Stangel, M. and Hartung H-P. "Remyelinating strategies for the treatment of multiple sclerosis" Prog Neurobiol., vol. 68, pp. 361-376 (2002).

Stevens, B. et al, "Adenosine: a neuron-glial transmitter promoting myelination in the CNS in response to action potentials" Neuron, vol. 36, pp. 855-868 (2002).

Studer L. et al. "Enhanced Proliferation, Survival, and Dopaminergic Differentiation of CNS Precursors in Lowered Oxygen" J. Neurosci., vol. 201, No. 19, pp. 7377-7383 (Oct. 1, 2000).

Sturrock, R. R. "Myelination of the mouse corpus callosum" Neuropathol Appl Neurobiol., vol. 6, pp. 415-420 (1980).

Szeligo, F. and Leblond, C. P. "Response of the three main types of glial cells of cortex and corpus callosum in rats handled during suckling or exposed to enriched, control and impoverished environments following weaning" J. Comp. Neurol., vol. 172, pp. 247-263 (1977).

Tang, D. G. et al. "Long-term culture of purified postnatal oligodendrocyte precursor cells. Evidence for an intrinsic maturation program that plays out over months" J. Cell Biol., vol. 148, pp. 971-984 (2000).

Tauber, H. et al. "Myelination in rabbit optic nerves is accelerated by artificial eye opening" Neuroci Lett., vol. 16, pp. 235-238 (1980).

The American Heritage Dictionary of the English Language 4th Ed., Dictionary.com/neural (2000).

Totoiu, M. O. and Keirstead, H. S. "Spinal cord injury is accompanied by chronic progressive demyelination" J Comp Neurol., vol. 486, pp. 373-383 (2005).

Tropepe, V. et al., "Transforming growth factor-α null and senescent mice show decreased neural progenitor cell proliferation in the forebrain subependyma", J. Neurosci., vol. 17, Issue 20, pp. 7850-7859 (1997).

Van Walderveen et al. "Magnetic resonance evaluation of disease activity during pregnancy in multiple sclerosis" Neurology, vol. 44, pp. 327-329 (1994).

Voskuhl, R. R. "Hormone-based therapies in MS" Int. MS J, vol. 10, pp. 60-66 (2003).

Walker, C. D. et al., "Mother to infant or infant to mother? Reciprocal regulation of responsiveness to stress in rodents and the implications for humans" J. Psy. Neurosci. vol. 29, No. 5, pp. 364-382 (2004).

Wardlaw, J.M. et al "is diffusion imaging appearance as independent predictor of outcome after ischemic stroke?" Neurology, vol. 59, pp. 1381-1387 (2002).

Waschek, J.A. "Multiple actions of pituitary adenylyl cyclase activating peptide in nervous system development and regeneration" Develop. Neuro., vol. 24, pp. 14-23, (2002).

Weetman, J.A. "The immunology of pregnancy" Thyroid, vol. 9, No. 7, pp. 643-646 (1999).

Whittemore et al., "Mitogen and substrate differentially affect the lineage restriction of adult subventricular zone neural precursor cell populations" Experimental Cell Research 252:75-95 (1999).

Wrighton, N.C., et al. "Small peptides as potent mimetics of the protein hormone erythropoietin" Sci., vol. 273, No. 5274, pp. 458-464 (1996).

Wu, H. Y. et al. "Expression of QKI proteins and MAP1B identifies actively myelinating oligodendrocytes in adult rat brain" Mol. Cell. Neurosci., vol. 17, pp. 292-302 (2001).

Arsenijevic et al., "Insulin-like growth factor-I is necessary for neural stem cell proliferation and demonstrates distinct actions of epidermal growth factor and fibroblast growth factor-2," Journal of Neuroscience, pp. 7194-7202 (2001).

Lobie et al., "Growth hormone, insulin-like growth factor I and the CNS: localization, function and mechanism of action," Growth Hormone & IGF Research, pp. S51-S56 (2000).

* cited by examiner

METHOD OF ENHANCING NEURAL STEM CELL PROLIFERATION, DIFFERENTIATION, AND SURVIVAL USING PITUITARY ADENYLATE CYCLASE ACTIVATING POLYPEPTIDE (PACAP)

RELATED APPLICATIONS

This application claims the benefit of U.S. Provisional Application Ser. No. 60/399,390, filed Jul. 31, 2002. The entire disclosure of this priority application is hereby incorporated by reference.

FIELD OF THE INVENTION

The present invention relates to a method of enhancing proliferation and differentiation of neural stem cells in vivo and in vitro using pituitary adenylate cyclase-activating peptide. In a preferred embodiment, additional growth factors are also utilized. The present invention has applications in the treatment of neurodegenerative diseases, such as Alzheimer's, Parkinson's, and Huntington's Diseases.

REFERENCES

U.S. Pat. No. 5,128,242.
U.S. Pat. No. 5,198,542.
U.S. Pat. No. 5,208,320.
U.S. Pat. No. 5,326,860.
U.S. Pat. No. 5,521,069.
U.S. Pat. No. 5,547,935.
U.S. Pat. No. 5,623,050.
U.S. Pat. No. 5,750,376.
U.S. Pat. No. 5,801,147.
U.S. Pat. No. 5,955,346.
U.S. Pat. No. 6,017,533.
U.S. Pat. No. 6,165,783.
U.S. Pat. No. 6,191,106.
U.S. Pat. No. 6,017,533.
U.S. Pat. No. 6,242,563.
U.S. Pat. No. 6,294,346.
U.S. Pat. No. 6,399,316.
U.S. Pat. No. 6,429,186.
International PCT Application No. WO 93/01275.
International PCT Application No. WO 94/10292.
International PCT Application No. WO 03/040310.
EPO Publication No. 0467279A3.

A. Arimura et al., "Perspectives on Pituitary Adenylate Cyclase Activating Polypeptide (PACAP) in the neuroendocrine, endocrine, and nervous systems" Jap. J. Physiol. 48:301–331 (1998).

A. Arimura et al., "Tissue distribution of PACAP as determined by RIA: highly abundant in the rat brain and testes," Endocrinol. 129:2787–2789 (1991).

A. Arimura et al., "PACAP functions as a neurotrophic factor," Ann. N.Y. Acad. Sci. 739:228–243 (1994).

W. A. Banks et al., "Passage of pituitary adenylate cyclase activating polypeptide 1–27 and pituitary adenylate cyclase activating polypeptide 1–38 acorss the blood-brain barrier," J. Pharmacol. Exp. Ther. 267(2):690–6 (1993).

S.A. Bayer, "Neuron production in the hippocampus and olfactory bulb of the adult rat brain: addition or replacement?" N.Y. Acad. Sci. 457:163–173 (1985).

S. Bernichtein et al., "S179D-human PRL, a pseudophosphorylated human PRL analog, is an agonist and not an antagonist," Endocrinology 142(9):3950–3963 (2001).

R. G. Carey et al., "Pituitary adenylate cyclase activating polypeptide antimitogenic signaling in cerebral cortical progenitors is regulated by p57Kip 2-dependent CDK2 activity," J. Neurosci. 22(5):1583–91 (2002).

J. Christophe, "Type I receptors for PACAP (a neuropeptide even more important than VIP?)" Biochim. Biophys. Acta 1154:183–99 (1993).

C. G. Craig et al., "In vivo growth factor expansion of endogenous subependymal neural precursor cell populations in adult mouse brain," J. Neurosci. 16(8):2649–58 (1996).

C. R. Freed et al., "Survival of implanted fetal dopamine cells and neurologic improvement 12 to 46 months after transplantation for Parkinson's Disease," N. Engl. J. Med. 327:1549–1555 (1992).

D. E. Hansel et al., "Regulation of olfactory neurogenesis by amidated neuropeptides," J. Neurosci. Res. 66:1–7 (2001).

H. Hashimoto et al., "Molecular cloning and tissue distribution of a receptor for pituitary adenylate cyclase-activating polypeptide," Neuron 11:333–342 (1993).

M. S. Kaplan, "Neurogenesis in the 3-month old rat visual cortex," J. Comp. Neurol. 195:323–338 (1981).

C. Kimura et al., "A novel peptide which stimulates adenylate cyclase: molecular cloning and characterization of the ovine and human cDNAs," Biochem. Biophys. Res. Comm. 166:81–89 (1990).

D. van der Kooy and S. Weiss, "Why stem cells?" Science 287:1439–41 (2000).

D. Lindholm et al., "Developmental regulation of pituitary adenylate cyclase activating polypeptide (PACAP) and its receptor 1 in rat brain: function of PACAP as a neurotrophic factor," Ann. N.Y. Acad. Sci. 865:189–96 (1998).

N. Lu and E. DiCicco-Bloom, "Pituitary adenylate cyclase-activating polypeptide is an autocrine inhiitor of mitosis in cultured cortical precursor cells," Proc. Natl. Acad. Sci. USA 94:3357–3362 (1997).

A. Miyata et al., "Isolation of a novel 38 residue-hypothalamic polypeptide which stimulates adenylate cyclase in pituitary cells," Biochem. Biophys. Res. Comm. 164:567–574 (1989).

C. Otto et al., "Altered emotional behavior in PACAP-type-I-receptor-deficient mice," Brain Res. Mol. Brain Res. 91(1-2):78–84 (2001).

M. J. Perlow et al., "Brain grafts reduce motor abnormalities produced by destruction of nigrostriatal dopamine system," Science 204:643–647 (1979).

C. S. Potten and Loeffler, "Stem cells: attributes, cycles, spirals, pitfalls and uncertainties. Lessons for and from the Crypt," Development 110:1001–1020 (1990).

P. Rakic, "Limits of neurogenesis in primates," Science 227:1054–1056 (1985).

B. A. Reynolds and S. Weiss, "Generation of neurons and astrocytes from isolated cells of the adult mammalian central nervous system," Science 255:1707–1710 (1992).

R. Rietze et al., "Mitotically active cells that generate neurons and astrocytes are present in multiple regions of the adult mouse hippocampus, " J. Comp. Neurol. 424(3):397–408 (2000).

T. Shingo et al., "Erythropoietin regulates the in vitro and in vivo production of neuronal progenitors by mammalian forebrain neural stem cells," J. Neurosci. 21(24):9733–9743 (2001).

D. D. Spencer et al., "Unilateral transplantation of human fetal mesencephalic tissue into the caudate nucleus of patients with Parkinson's Disease," N. Engl. J. Med. 327:1541–1548 (1992).

D. Vaudry et al., "Pituitary adenylate cyclase-activating polypeptide and its receptors: from structure to functions," Pharmacol. Rev. 52:269–324 (2000).

J. A. Waschek, "VIP and PACAP receptor-mediated actions on cell proliferation and survival," Ann. N.Y. Acad. Sci. 805:290–300 (1996).

H. Widner et al., "Bilateral fetal mesencephalic grafting into two patients with Parkinsonism induced by 1-methyl-4-phenyl-1,2,3,6-tetrahydropyridine (MPTP)," N. Engl. J. Med. 327:1556–1563 (1992).

A. Yuhara et al., "PACAP has a neurotrophic effect on cultured basal forebrain cholinergic neurons from adult rats," Brain Res. Dev. Brain Res. 131(1):41–5 (2001).

All of the publications, patents, and patent applications cited in this application are hereby incorporated by reference in their entirety to the same extent as if the disclosure of each individual publication, patent, or patent application was specifically and individually indicated to be incorporated by reference in its entirety.

BACKGROUND OF THE INVENTION

Neurogenesis in mammals is largely complete early in the postnatal period. While it was previously thought that cells of the adult mammalian central nervous system (CNS) have little or no ability to undergo mitosis and generate new neurons, recent studies have demonstrated that the mature nervous system does have some limited capability to produce new neurons. (Craig, et al., 1996; Rietze, et al., 2000; review in van der Kooy and Weiss, 2000). Several mammalian species (e.g., rats) exhibit the limited ability to generate new neurons in restricted adult brain regions such as the dentate gyrus and olfactory bulb (Kaplan, 1981; Bayer, 1985). However, the generation of new CNS neurons in adult primates does not normally occur (Rakic, 1985). This relative inability to produce new neural cells in most mammals (and especially primates) may be advantageous for long-term memory retention; however, it is a distinct disadvantage when the need to replace lost neuronal cells arises due to an injury or disease.

The role of neural stem cells in the adult is to replace cells that are lost by natural cell death, injury or disease. Until recently, the low turnover of cells in the mammalian CNS together with the inability of the adult mammalian CNS to generate new neuronal cells in response to the loss of cells following an injury or disease had led to the assumption that the adult mammalian CNS does not contain multipotent neural stem cells. The critical identifying feature of a stem cell is its ability to exhibit self-renewal or to generate more of itself. The simplest definition of a stem cell would be a cell with the capacity for self-maintenance. A more stringent (but still simplistic) definition of a stem cell is provided by Potten and Loeffler (1990) who have defined stem cells as "undifferentiated cells capable of a) proliferation, b) self-maintenance, c) the production of a large number of differentiated functional progeny, d) regenerating the tissue after injury, and e) a flexibility in the use of these options."

CNS disorders encompass numerous afflictions such as neurodegenerative diseases (e.g., Alzheimer's and Parkinson's), acute brain injury (e.g., stroke, head injury, cerebral palsy) and a large number of CNS dysfunctions (e.g., depression, epilepsy, and schizophrenia). In recent years, neurodegenerative disease has become an important concern due to the expanding elderly population which is at the greatest risk for these disorders. These diseases, which include Alzheimer's Disease, Parkinson's Disease, Huntington's Disease, Multiple Sclerosis (MS), and Amyotrophic Lateral Sclerosis, have been linked to the degeneration of neuronal cells in particular locations of the CNS, leading to the inability of these cells or the brain region to carry out their intended function.

Degeneration in a brain region known as the basal ganglia can lead to diseases with various cognitive and motor symptoms, depending on the exact location. The basal ganglia consists of many separate regions, including the striatum (which consists of the caudate and putamen), the globus pallidus, the substantia nigra, substantia innominate, ventral pallidum, nucleus basalis of Meynert, ventral tegmental area and the subthalamic nucleus. Many motor deficits are a result of neuronal degeneration in the basal ganglia. Huntington's Chorea is associated with the degeneration of neurons in the striatum, which leads to involuntary jerking movements in the host. Degeneration of a small region called the subthalamic nucleus is associated with violent flinging movements of the extremities in a condition called ballismus, while degeneration in the putamen and globus pallidus is associated with a condition of slow writhing movements or athetosis. In the case of Parkinson's Disease, degeneration is seen in another area of the basal ganglia, the substantia nigra pars compacta. This area normally sends dopaminergic connections to the dorsal striatum which are important in regulating movement. In the case of Alzheimer's Disease, there is a profound cellular degeneration of the forebrain and cerebral cortex. In addition, upon closer inspection, a localized degeneration in an area of the basal ganglia, the nucleus basalis of Meynert, appears to be selectively degenerated. This nucleus normally sends cholinergic projections to the cerebral cortex which are thought to participate in cognitive functions including memory. Other forms of neurological impairment can occur as a result of neural degeneration, such as cerebral palsy, or as a result of CNS trauma, such as stroke and epilepsy.

In addition to neurodegenerative diseases, brain injuries often result in the loss of neurons, the inappropriate functioning of the affected brain region, and subsequent behavior abnormalities. Probably the largest area of CNS dysfunction (with respect to the number of affected people) is not characterized by a loss of neural cells but rather by an abnormal functioning of existing neural cells. This may be due to inappropriate firing of neurons, or the abnormal synthesis, release, and/or processing of neurotransmitters. These dysfunctions may be the result of well studied and characterized disorders such as depression and epilepsy, or less understood disorders such as neurosis and psychosis.

Demyelination of central and peripheral neurons occurs in a number of pathologies and leads to improper signal conduction within the nervous system. Myelin is a cellular sheath, formed by glial cells, that surrounds axons and axonal processes that enhances various electrochemical properties and provides trophic support to the neuron. Myelin is formed by Schwann cells in the peripheral nervous system and by oligodendrocytes in the central nervous system. Among the various demyelinating diseases, MS is the most notable.

To date, treatment for CNS disorders has been primarily via the administration of pharmaceutical compounds. Unfortunately, this type of treatment has been fraught with many complications including limited ability to transport drugs across the blood-brain barrier and drug-tolerance acquired by patients to whom these drugs are administered long-term. For instance, partial restoration of dopaminergic activity in Parkinson's patients has been achieved with levodopa, which is a dopamine precursor able to cross the blood-brain barrier. However, patients become tolerant to the effects of levodopa, and therefore, steadily increasing dosages are needed to maintain its effects. In addition, there are a number of side effects associated with levodopa such as increased and uncontrollable movement.

Recently, the concept of neurological tissue grafting has been applied to the treatment of neurological diseases such as Parkinson's Disease. Neural grafts may avert the need not only for constant drug administration, but also for complicated drug delivery systems which arise due to the blood-brain barrier. However, there are limitations to this technique as well. First, cells used for transplantation which carry cell surface molecules of a differentiated cell from another host can induce an immune reaction in the host. In addition, the cells must be at a stage of development where they are able to form normal neural connections with neighboring cells. For these reasons, initial studies on neurotransplantation centered on the use of fetal cells. Several studies have shown improvements in patients with Parkinson's Disease after receiving implants of fetal CNS tissue. Implantation of embryonic mesencephalic tissue containing dopamine cells into the caudate and putamen of human patients was shown by Freed et al. (1992) to offer long-term clinical benefit to some patients with advanced Parkinson's Disease. Similar success was shown by Spencer et al. (1992). Widner et al. (1992) have shown long-term functional improvements in patients with N-methyl-4-phenyl-1,2,3,6-tetrathydropyridine (MPTP)-induced Parkinsonism that received bilateral implantation of fetal mesencephalic tissue. Perlow et al. (1979) describe the transplantation of fetal dopaminergic neurons into adult rats with chemically induced nigrostriatal lesions. These grafts showed good survival, axonal outgrowth and significantly reduced the motor abnormalities in the host animals. A further discussion of tissue transplantation techniques and drawbacks can be found in U.S. Pat. No. 6,294,346 B1.

While the studies noted above are encouraging, the use of large quantities of aborted fetal tissue for the treatment of disease raises ethical considerations and political obstacles. There are other considerations as well. Fetal CNS tissue is composed of more than one cell type, and thus is not a well-defined source of tissue. In addition, there are serious doubts as to whether an adequate and constant supply of fetal tissue would be available for transplantation. For example, in the treatment of MPTP-induced Parkinsonism (Widner, 1992) tissue from 6 to 8 fresh fetuses were required for implantation into the brain of a single patient. There is also the added problem of the potential for contamination during fetal tissue preparation. Moreover, the tissue may already be infected with a bacteria or virus, thus requiring expensive diagnostic testing for each fetus used. However, even diagnostic testing might not uncover all infected tissue. For example, the successful diagnosis of HIV-free tissue is not guaranteed because antibodies to the virus are generally not present until several weeks after infection.

While currently available transplantation approaches represent a significant improvement over other available treatments for neurological disorders, they suffer from significant drawbacks. The inability in the prior art of the transplant to fully integrate into the host tissue, and the lack of availability of neuronal cells in unlimited amounts from a reliable source for grafting are, perhaps, the greatest limitations of neurotransplantation. A well-defined, reproducible source of neural cells is currently available. It has been discovered that multipotent neural stem cells, capable of producing progeny that differentiate into neurons and glia, exist in adult mammalian neural tissue. (Reynolds and Weiss, 1992). Methods have been provided for the proliferation of these stem cells to provide large numbers of neural cells that can differentiate into neurons and glia (See, e.g., U.S. Pat. No. 5,750,376, and International Application No. WO 93/01275). Various factors can be added to neural cell cultures to influence the make-up of the differentiated progeny of multipotent neural stem cell, as disclosed in published PCT application WO 94/10292. Additional methods for directing the differentiation of stem cell progeny were disclosed in U.S. Pat. No. 6,165,783 utilizing erythropoietin and various growth factors.

Thus, it can be seen that a need exists for the repair of damaged neural tissue in a relatively non-invasive fashion, by inducing neural cells to proliferate and differentiate into neurons, astrocytes, and oligodendrocytes in vivo, averting the need for transplantation. Additional methods for increasing the number of neural stem cells and their progeny in vitro are also desirable both for research and for transplantation. As the adult nervous system possesses limited capacity for reproducing new neurons, it is particularly desirable to be able to enhance proliferation of neural stem cells in order to be able to replace lost or damaged neurons.

SUMMARY OF THE INVENTION

Accordingly, a major object of the present invention is to provide both in vivo and in vitro techniques of enhancing neural stem cell proliferation and/or survival and/or differentiation. The present inventors have now found that PACAP can enhance neural stem cell proliferation, survival, and differentiation both in vitro and in vivo in embryonic and adult tissue.

The present invention provides a method for increasing neural stem cell and/or neural stem cell progeny number comprising adding pituitary adenylate cyclase-activating polypeptide (PACAP) to multipotent neural stem cells in an amount effective to increase neural stem cells and/or neural stem cell progeny number. In one embodiment, PACAP38 is used. In another embodiment, PACAP27 is used. In one embodiment, the number of neural stem cells and/or neural stem cell progeny is increased by enhancing proliferation. In an alternative embodiment, the number of neural stem cells and/or progeny is increased by enhancing survival. In another alternative, the number of neural stem cells and/or progeny is increased by increasing the number of secondary neural stem cells obtained from a primary neural stem cell.

In one embodiment, the neural stem cells are located in a subject. Preferably, the subject is a mammal, particularly a human. Even more preferably, the subject is an adult. In one embodiment, the subject is suffering from a neurodegenerative disease or brain injury. In a preferred embodiment, the subject is suffering from Alzheimer's Disease, Parkinson's Disease, Huntington's Disease, or stroke. The number of neural stem cells and/or progeny are preferably increased in the subventricular zone of the subject. In one embodiment, the neural stem cells and/or progenitor cells which are derived from neural stem cells are transplanted into the subject.

In a preferred embodiment, at least one growth factor is added in addition to PACAP. In a particularly preferred embodiment, the growth factor is fibroblast growth factor-2 (FGF-2), with or without heparan sulfate. In another particularly preferred embodiment, the growth factor is epidermal growth factor, EGF. In still another preferred embodiment, prolactin is used.

In one embodiment the growth factor is added to the cells concurrently with PACAP. In another embodiment, the growth factor is added sequentially with the PACAP. In a particularly preferred embodiment, the PACAP is added prior to the growth factor. In another particularly preferred embodiment, PACAP is added after the growth factor.

Another aspect of the present invention provides a method of increasing the number of neural stem cells and/or neurospheres comprising adding PACAP to a neural stem cell culture to increase the number of neural stem cells and/or neurospheres generated from the neural stem cell culture. In one embodiment, PACAP38 is used. In another embodiment, PACAP27 is used. In a preferred embodiment, the neural stem cell culture is a primary culture or a clonal density culture. In another embodiment, the method further comprises adding a growth factor to the neural stem cell culture. In a preferred embodiment the growth factor is FGF-2, with or without heparan sulfate. In another preferred embodiment, the growth factor is EGF. In still another preferred embodiment, the growth factor is prolactin.

In yet another aspect, the present invention provides a method of enhancing proliferation and/or differentiation and/or survival of neural stem cells in a subject comprising administering PACAP to the subject in an amount sufficient to enhance proliferation and/or differentiation and/or survival of neural stem cells. In one embodiment, PACAP38 is used. In another embodiment, PACAP27 is used. In one embodiment, the differentiation into neurons is increased.

In a preferred embodiment, the subject is a mammal. In more preferred embodiment, the mammal is an adult. In a particularly preferred embodiment, the mammal is a human. In a preferred embodiment, at least one growth factor is administered. In particularly preferred embodiment, the growth factor is FGF-2 (with or without heparan sulfate), EGF, or prolactin.

In one embodiment, the subject is suffering from a neurodegenerative disease or brain injury. In a particularly preferred embodiment, the subject is suffering from Alzheimer's Disease, Parkinson's Disease, Huntington's Disease, or stroke. In a preferred embodiment, the proliferation and/or differentiation and/or survival of neural stem cells occurs in the subventricular zone. In a particularly preferred embodiment, the multipotent neural stem cells and/or progenitor cells which are derived from said multipotent neural stem cells are transplanted into said subject.

In one embodiment, the growth factor is administered concurrently with PACAP. In another embodiment, the growth factor is administered consecutively with PACAP. In a particularly preferred embodiment, the growth factor is administered prior to PACAP. In another embodiment, the growth factor is administered after PACAP.

DETAILED DESCRIPTION OF THE INVENTION

Figure 1:
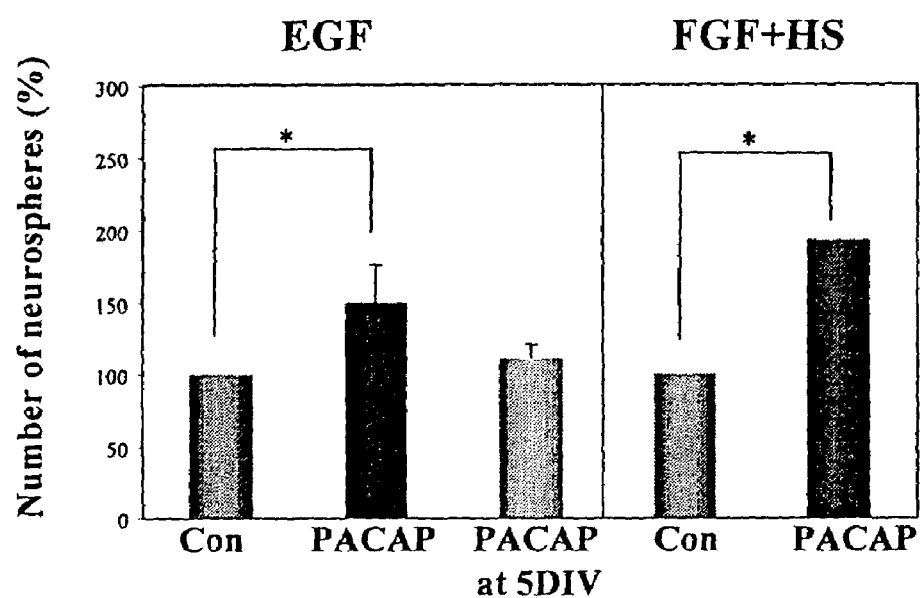
FIG. 1. Pituitary adenylate cyclase-activating polypeptide (PACAP) enhanced neural stem cell survival in vitro. Embryonic day 14 ganglionic eminences (E14 GE) were dissociated and plated at 150 cells/ml in the indicated growth factor conditions. The number of neurospheres was counted after 10 days. Data are expressed relative to the number obtained with epidermal growth factor (EGF) alone (100%). PACAP increased the number of neurospheres obtained with either EGF or fibroblast growth factor (FGF)+heparan sulfate (HS). Delayed addition of PACAP did not increase neurosphere number, indicating that PACAP acts as a survival factor. (* $p<0.05$, n=3).

The present invention relates to a method of increasing the number of neural stem cells or neural stem cell progeny by adding PACAP and optionally one or more growth factors to neural stem cells and/or progeny. The numbers of neural stem cell and neural stem cell progeny may be increased by a variety of mechanisms, including increasing proliferation, increasing survival, and increasing the number of secondary neurospheres that can be derived from primary neurospheres. These methods may be practiced both in vivo and in vitro. With regard to in vitro methods, the number of neural stem cells and/or neurospheres can be increased by exogenously adding PACAP to neural stem cell cultures.

Additionally, the present invention provides for a method of enhancing the differentiation of neural stem cells in a subject. In particular, PACAP can increase the differentiation of neural stem cells into neurons. The present invention has important implications for the treatment and research of neurodegenerative diseases and brain injury.

Prior to describing the invention in further detail, the terms used in this application are defined as follows unless otherwise indicated.

As used herein, the term "multipotent neural stem cell" (or more simply, neural stem cell) refers to an undifferentiated cell which is capable of self-maintenance. Thus, in essence, a stem cell is capable of dividing without limit. "Progenitor cells" are non-stem cell progeny of a multipotent neural stem cell. A distinguishing feature of a progenitor cell is that, unlike a stem cell, it has limited proliferative ability and thus does not exhibit self-maintenance. It is committed to a particular path of differentiation and will, under appropriate conditions, eventually differentiate. A neuronal progenitor cell is capable of a limited number of cell divisions before giving rise to differentiated neurons. A glial progenitor cell likewise is capable of a limited number of cell divisions before giving rise to astrocytes or oligodendrocytes. A neural stem cell is multipotent because its progeny include both neuronal and glial progenitor cells and thus is capable of giving rise to neurons, astrocytes, and oligodendrocytes. Multipotent stem cell progeny thus include neuronal precursor cells, glial precursor cells, neurons, and glial cells.

A "neurosphere" is a group of cells derived from a single neural stem cell as the result of clonal expansion. Primary neurospheres are generated by plating as primary cultures brain tissue which contains neural stem cells. The method for culturing neural stem cells to form neurospheres has been described in, e.g., U.S. Pat. No. 5,750,376. Secondary neurospheres can be generated by dissociating primary neurospheres and allowing the individual dissociated cells to form neurospheres again.

"PACAP" or "pituitary adenylate cyclase activating polypeptide" is a polypeptide hormone that activates adenylate cyclase. The native mammalian PACAP is a 38 or 27 amino acid polypeptide hormone which is released by the hypothalamus. As used herein, "PACAP" encompasses polypeptides which share substantial sequence similarity with either form of the native mammalian PACAP and possess a biological activity of the native mammalian PACAP. Having a biological activity of native mammalian PACAP means having at least one activity of a native mammalian PACAP, such as binding to one or more of the same receptors as the native mammalian PACAP binds and/or stimulating adenylate cyclase. Preferably, the PACAP binds to one of more of the same receptors as the native mammalian PACAP. PACAP can be isolated from the pituitary or can be synthesized using genetic engineering or chemical synthetic techniques.

A polypeptide which shares "substantial sequence similarity" with a native mammalian PACAP is at least about 30% identical with native mammalian PACAP at the amino acid level. The PACAP is preferably about 40%, more preferably about 60%, yet more preferably at least about 70%, and most preferably, at least about 80% identical with the native mammalian PACAP at the amino acid level. Thus, the term PACAP encompasses PACAP analogs which are deletional, insertional, or substitutional mutants of the native mammalian PACAP. Furthermore, the term PACAP encompasses PACAPs from other species and the naturally occurring and synthetic variants thereof. Particularly useful are the analogs and variants disclosed in, e.g., U.S. Pat. Nos. 5,128,242; 5,198,542; 5,208,320; 5,326,860; 5,623,050; 5,801,147; and 6,242,563.

"Percent identity" or "% identity" refers to the percentage of amino acid sequence in a protein or polypeptide which are also found in a second sequence when the two sequences are aligned. Percent identity can be determined by any methods or algorithms established in the art, such as LALIGN or BLAST.

By "growth factor" is meant a substance that affects the growth of a cell or an organism, including proliferation, differentiation, and increases in cell size. A growth factor is a polypeptide which shares substantial sequence identity with a native mammalian growth factor and possesses a biological activity of the native mammalian growth factor. In a preferred embodiment, the native mammalian growth factor is a native human growth factor. Having a biological activity of a native mammalian growth factor means having at least one activity of a native mammalian growth factor, such as binding to the same receptor as a particular native mammalian growth factor binds and/or eliciting proliferation and/or differentiation and/or changes in cell size. Preferably, the growth factor binds to the same receptor as a particular native mammalian growth factor. This includes functional variants of the native mammalian growth factor.

A polypeptide which shares "substantial sequence similarity" with the native mammalian growth factor is at least about 30% identical to the native mammalian growth factor at the amino acid level. The growth factor is preferably at least about 40%, more preferably at least about 60%, and most preferably about 60% identical to the native mammalian growth factor at the amino acid level. Thus, the term growth factor encompasses analogs which are deletional, insertional, or substitutional mutants of a native mammalian growth factor. Furthermore, the term growth factor encompasses the growth factors from other species and naturally occurring and synthetic variants thereof. Exemplary growth factors include platelet-derived growth factor (PDGF), epidermal growth factor (EGF), erythropoeitin, insulin-like growth factor-1 and -2 (IGF-1, IGF-2), transforming growth factors $\alpha$ and $\beta$ (TGF-$\alpha$, TGF-$\beta$), acidic and basic fibroblast growth factors (a-FGF/FGF-2, b-FGF/FGF-2), interleukins 1, 2, 6, and 8 (IL-1, IL-2, IL-6, IL-8), nerve growth factor (NGF), brain-derived neurotrophic factor (BDNF), neurotrophin-3 (NT-3), interleukin-3, hematopoietic colony stimulating factors (CSFs), amphiregulin, interferon-$\gamma$ (INF-$\gamma$), thyrotropin releasing hormone (TRH), and prolactin.

It should be noted that variants or analogs of these agents, which share a substantial identity with a native mammalian growth factor listed above and are capable of binding to a receptor of the native mammalian growth factor can be used in the present application. For example, EGF variants or analogs, which share a substantial identity with a native mammalian EGF and are capable of binding to a receptor of a native mammalian growth factor, can be used in the present application. These EGF variants and analogs include, but are not limited to, the recombinant modified EGF having a deletion of the two C-terminal amino acids and a neutral amino acid substitution at position 51, such as asparagine, glutamine, serine, or alanine (particularly EGF51N or EGF51Q, having asparagine (N) or glutamine (Q) at position 51, respectively; WO 03/040310); the EGF mutein (EGF-X16) in which the His residue at position 16 is replaced with a neutral or acidic amino acid (U.S. Pat. No. 6,191,106); the 52-amino acid deletion mutant of EGF which lacks the amino terminal residue of the native EGF (EGF-D); the EGF deletion mutant in which the amino terminal residue as well as the two C-terminal residues (Arg-Leu) are deleted (EGF-B); the EGF-D in which the Met residue at position 21 is oxidized (EGF-C); the EGF-B in which the Met residue at position 21 is oxidized (EGF-A); heparin-binding EGF-like growth factor (HB-EGF); betacellulin; amphiregulin; neuregulin; or a fusion protein comprising any of the above. Other useful EGF analogs or variants are described in WO 03/040310, and U.S. Pat. Nos. 6,191,106 and 5,547,935.

Specifically included as prolactins are the naturally occurring prolactin variants, prolactin-related protein, placental lactogens, S179D-human prolactin (Bernichtein et al., 2001), prolactins from various mammalian species, including, but not limited to, human, other primates, rat mouse, sheep, pig, and cattle, and the prolactin mutants described in U.S. Pat. Nos. 6,429,186 and 5,955,346.

To "enhance" neural stem cell proliferation, differentiation, or survival means to increase the amount or rate of these parameters in the presence of the substance compared to the amount or rate in the absence of the substance. For example, PACAP enhances proliferation of neural stem cells by increasing the number of mitotic cells in a population of neural stem cells compared to the number of mitotic cells in the absence of PACAP.

A "neurodegenerative disease or condition" is a disease or a medical condition associated with neuron loss or dysfunction. Examples of neurodegenerative diseases or conditions include neurodegenerative diseases, brain injuries or CNS dysfunctions. Neurodegenerative diseases include, e.g., Alzheimer's Disease, Multiple Sclerosis, Huntington's Disease, Amyotrophic Lateral Sclerosis, and Parkinson's Disease. Brain injuries include, e.g., injuries to the nervous system due to surgery, stroke, and physical accidents. CNS dysfunctions include, e.g., depression, epilepsy, neurosis, and psychosis.

"Treating or ameliorating" means the reduction or complete removal of the symptoms of a disease or medical condition.

An "effective amount" is an amount of a therapeutic agent sufficient to achieve the intended purpose. For example, an effective amount of a growth factor or PACAP to enhance the proliferation of neural stem cells is an amount sufficient, in vivo or in vitro, to result in an enhancement in proliferation of neural stem cells over the speed or number of cells in the absence of the growth factor or PACAP. An effective amount of a growth factor or PACAP to treat or ameliorate a neurodegenerative disease or condition is an amount of the growth factor or PACAP sufficient to reduce or remove the symptoms of the neurodegenerative disease or condition. The effective amount of a given therapeutic agent will vary with factors such as the nature of the agent, the route of administration, the size and species of the animal or subject to receive the therapeutic agent, and the purpose of administration. The effective amount in each individual case may be determined empirically by a skilled artisan according to established methods in the art.

DETAILED DESCRIPTION

PACAP was first discovered from the hypothalami of sheep as a peptide promoting adenylate cyclase activity of the pituitary gland. (Miyata et al., 1989; U.S. Pat. No. 5,128,242). The particular PACAP first isolated was a peptide consisting of 38 amino acid residues called PACAP38. However, a 27 amino acid variant of PACAP was also discovered (PACAP27). Both peptides are relatively equal in the ability to stimulate adenylate cyclase. The expression of a PACAP of similar structure to that isolated from sheep was found in humans, suggesting an important evolutionary role due to conservation. (Kimura et al., 1990; Arimura et al., 1998; Vaudry et al., 2000).

PACAP peptides have been found in a number of diverse tissues, including the brain, pituitary gland, the testes, and the adrenal gland. (Arimura et al., 1991). Several PACAPs have been found and described in various publications, including U.S. Pat. No. 5,128,242 and EPO Publication No. 0467279A3). The genes for the PACAP38 and PACAP27 peptides have been isolated as described in U.S. Pat. No. 5,326,860 and U.S. Pat. No. 5,521,069. PACAP receptors have been described, e.g., in U.S. Pat No. 6,399,316 B1. At least three types of PACAP receptors have been identified. (Arimura et al, 1998). PACAP type 1 ($PAC_1$-R) receptors are expressed at high levels in the brain but low levels in the rest of the body. Type I PACAP receptors may stimulate adenylate cyclase (AC), phospholipase C (PLC), mitogen-activated protein kinase (MAPK), and calcium mobilization. (Christophe, 1993; Hashimoto et al., 1993; Arimura et al., 1998; D. Vaudry et al., 2000). Exemplary agonists and antagonists for the PACAP type I receptors are disclosed in U.S. Pat. No. 6,017,533.

The role of PACAP in the nervous system has been studied over the past decade. PACAP has been identified in numerous brain regions, including the hypothalamus, the nucleus accumbens, septum, cerebral cortex, midbrain, pons, medulla oblongata, amygdala, globus pallidus, thalamus, and posterior pituitary. (Arimura et al., 1998). It is now recognized that PACAP plays many diverse roles in the brain, including neurotrophic factor, neurotransmitter, neuromodulator, and neuroprotective agent. (For review, see Arimura et al., 1998; also Carey et al., 2002; Yuhara et al., 2001; Otto et al., 2001; Hansel et al., 2001; Arimura et al., 1994; Waschek, 1996; Lindholm et al., 1998). For example, PACAP can decrease mitosis in embryonic rat cortical precursors. (Lu and DiCicco-Bloom, 1997). In contrast, transfection of embryonic rat cortical cells with a splice variant of $PAC_1$-R resulted in increased proliferation.

In the present invention, methods of increasing neural stem cell number, survival, self-renewal, proliferation, and differentiation were discovered. As discussed in more detail in the Example below, PACAP is able to elicit these effects both in vivo and in vitro.

In addition to PACAP, other growth factors such as those described above can be used to augment the effects of PACAP. In particular, FGF (optionally with heparan sulfate) and EGF are particularly preferred embodiments. However, other growth factors, such as prolactin, are also useful. The PACAP may be administered sequentially or simultaneously with the other growth factor. The growth factor may be administered or added either before or after the administration or addition of PACAP.

For in vivo administration, compositions containing PACAP and/or other growth factors can be delivered via any route known in the art, such as orally, or parenterally, e.g., intravascularly, intramuscularly, transdermally, subcutaneously, or intraperitoneally. In a preferred embodiment, the composition is administered parenterally. The composition may be delivered directly into the CNS. Direct administration into the CNS can be accomplished via delivery into a ventricle, such as the lateral ventricle. However, PACAP is known to cross the blood-brain-barrier (Banks, 1993), making direct CNS administration unnecessary.

According to embodiments of the invention, PACAP may be administered in vivo to treat subjects suffering from neurodegenerative diseases, brain injuries, or CNS dysfunctions. Alzheimer's Disease, Huntington's Disease, and Parkinson's Disease, inter alia, may be treated according to various embodiments of the invention. Alternatively, the subject may be suffering from a stroke. Because of the prevalence of neurodegenerative diseases in adults, the preferred subject is an adult human. However, it is contemplated that younger subjects may also suffer from neurodegenerative disease, or more commonly, traumatic brain injury, and thus will benefit from the present invention. Additionally, while humans are particularly preferred subject, other species, such as those kept as pets, may also be treated according to an embodiment of the invention. Subjects may be treated with PACAP, and optionally, other growth factors, or neural stem cells may be exogenously treated and then transplanted into the subject. A combination of these approaches is also possible.

For in vitro practice of the present invention, multipotent neural stem cells can be obtained from embryonic, juvenile, or adult mammalian neural tissue (e.g. mouse and other rodents, and humans and other primates) or from other sources as described in PCT application WO 93/01275 and U.S. Pat. Nos. 5,750,376 and 6,294,346 B1.

In the absence of substrates that promote cell adhesion (e.g. ionically charged surfaces such as poly-L-lysine and poly-L-ornithine coated and the like), multipotent neural stem cell proliferation can be detected by the formation of clusters of undifferentiated neural cells termed "neurospheres", which after several days in culture, lift off the floor of the culture dish and float in suspension. Each neurosphere results from the proliferation of a single multipotent neural stem cell and is comprised of daughter multipotent neural stem cells and neural progenitor cells. The neurospheres can be dissociated to form a suspension of undifferentiated neural cells and transferred to fresh growth-factor containing medium. This reinitiates proliferation of the stem cells and the formation of new neurospheres. In this manner, an unlimited number of undifferentiated neural stem cell progeny can be produced by the continuous culturing and passaging of the cells in suitable culture conditions.

The ability to manipulate the fate of the differentiative pathway of the multipotent neural stem cell progeny to produce more neuronal progenitor cells and neurons is beneficial. Cell cultures that contain a higher percentage of neuronal progenitor cells and/or neurons will be useful for screening the effects of various drugs and other agents on neuronal cells. Methods for screening the effect of drugs on cell cultures are well known in the art and are also disclosed in U.S. Pat. Nos. 5,750,376 and 6,294,346 B1.

Cell cultures with an enriched neuronal-progenitor cell and/or neuron population can be used for transplantation to treat various neurological injuries, diseases or disorders. The neuronal progenitor cells or neurons or a combination thereof can be harvested and transplanted into a patient needing neuronal augmentation. Neuronal progenitor cells are particularly suitable for transplantation because they are still undifferentiated and, unlike differentiated neurons, there are no branched processes which can be damaged during transplantation procedures. Once transplanted, the neuronal progenitor cells differentiate in situ into new, functioning neurons. Suitable transplantation methods are known in the art and are disclosed in U.S. Pat. Nos. 5,750,376 and 6,294,346 B1.

Alternatively, a patient's endogenous multipotent neural stem cells could be induced to proliferate, differentiate, or survive in situ by administering to the patient a composition comprising PACAP and optionally one or more growth factors which instructs the neural stem cells to proliferate and to produce neuronal progenitor cells which eventually differentiate into neurons and to enhance differentiation and survival. Suitable methods for administering a composition to a patient which induces the in situ proliferation of the patient's stem cells are disclosed in U.S. Pat. Nos. 5,750,376 and 6,294,346 B1.

EXAMPLES

PACAP Regulates Neural Stem Cell Fate in Vitro and in Vivo

PACAP Receptor Expression.

As the PACAP receptor ($PAC_1$-R) is expressed in the forebrain germinal zone of the rat throughout early development, it is believed to play a role in regulating neural stem cells. Receptor expression was examined both in vitro and in vivo at various stages. Primary embryonic neural stem cells were isolated from the E14 ganglionic eminences as previously described (Reynolds and Weiss, 1992). Using Reverse-transcriptase PCR (RT-PCR) analysis, PACAP and $PAC_1$-R were found to be expressed in the embryonic day 14 murine ganglionic eminence (E14 GE). PAC1-R was also expressed in E14 EGF-generated neurospheres, further indicating a role in neural stem cell regulation.

The expression of PAC1-R was confirmed by Western blot analysis using ECL Plus (Amersham Biosciences). Anti-PAC1-R (1:1000) was obtained as a gift from Dr. Arimura. Western blots demonstrated that PAC1-R receptor protein expression was found in E14 and adult neurospheres, E14 ganglionic eminence, and the adult olfactory bulb and subventricular zone (data not shown). Immunohistochemistry was performed using TSA Fluorescence System (Perkin Elmer). Indirect immunocytochemistry showed PAC1-R immunoreactive cells in embryonic and adult neurospheres, in the E14 mouse GE and in the adult SVZ (data not shown). Because PAC1-R expression was observed in these various tissues in vitro and in vivo, PACAP may play an important role in regulating development and function of neural stem cells and/or neural stem cell progeny.

In Vitro Effects of PACAP.

General Methods.

Cell Culture: Primary embryonic neural stem cells were isolated from E14 ganglionic eminence as previously described (Reynolds and Weiss, 1992). Neurospheres were grown in the presence of EGF (20 ng/ml) or FGF-2 (20 ng/ml)+heparan sulfate (2 µg/ml) growth medium. Passaged neural stem cells were grown at a clonal density (150 cells/ml).

Single Cell Dissociation Assay: Single neurospheres (200 mm) were dissociated mechanically and then plated in a 96 well plate and incubated for 10 days in vitro in the presence of growth factors.

Differentiation of Neurospheres: Neurospheres were plated onto poly-L-ornithine coated coverslips in serum-free medium and subjected to immunocytochemistry after 5 days in vitro. The number of β-III tubulin-positive cells were counted.

PACAP Enhances Neural Stem Cell Survival.

E14 GE were dissociated and plated at 150 cells/ml in EGF, EGF+PACAP, FGF+HS, or FGF+HS+PACAP. The number of neurospheres were counted after 10 days. As shown in FIG. 1, the addition of PACAP significantly increased the number of primary neurospheres generated in response to FGF-2. PACAP also increased the number of primary neurospheres generated in response to EGF, but to a lesser extent than that observed with FGF-2. The addition of PACAP increased neurosphere number when added at the beginning of the culture period, but not when delayed until 5 days in vitro, indicating that PACAP enhances neural stem cell survival.

PACAP Increases Neural Stem Cell Self-Renewal.

Figure 2:
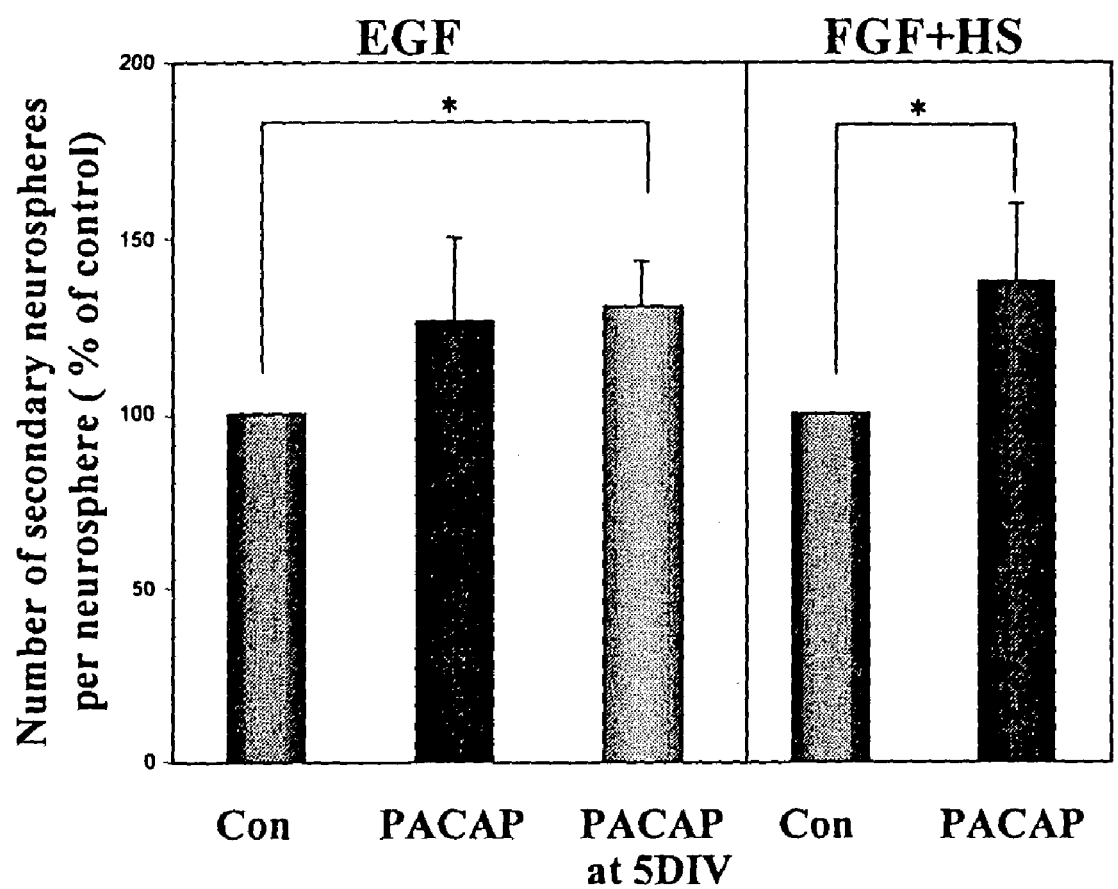
FIG. 2. PACAP increased neural stem cell self-renewal in vitro. Primary E14 neurospheres were grown in the indicated conditions, dissociated, and replated in the presence of either EGF or FGF+HS. Neurospheres were counted and data were normalized to either EGF or FGF+HS alone. PACAP increased the number of secondary neurospheres obtained with either EGF or FGF+HS. (* $p<0.05$, n=3).

Primary E14 neurospheres were grown in the indicated conditions in FIG. 2, then dissociated and replated in the presence of either EGF or FGF+HS and the number of secondary neurospheres was counted. Data were normalized to the numbers of secondary neurospheres generated from primary neurospheres grown in the absence of PACAP. As shown in FIG. 2, the number of secondary neurospheres generated by single primary neurospheres grown in the presence of PACAP significantly increased, indicating that PACAP enhances neural stem cell expansion/self-renewal.

PACAP Enhances in Vitro Neurogenesis by Neural Stem Cells.

Figure 3:
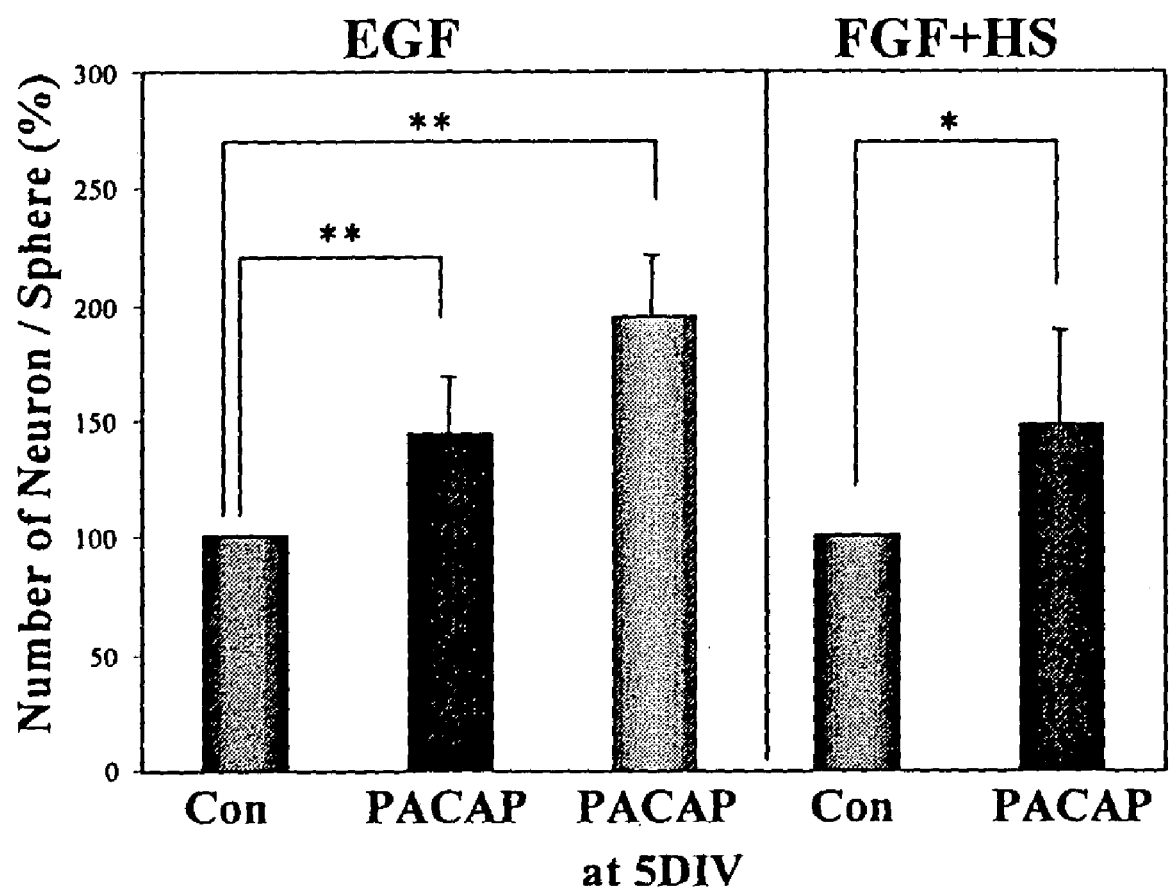
FIG. 3. PACAP enhanced in vitro neurogenesis by neural stem cells. Primary E14 neurospheres were grown in the indicated conditions for seven days and then processed for immunocytochemistry to count the number of B-tubulin immunopositive neurons. Data were normalized to either EGF or FGF+HS alone (100%). PACAP increased the number of neurons in all conditions. (* $p<0.01$, n=3).

Primary E14 neurospheres were grown in either EGF or FGF media in the presence or absence of PACAP for seven days, differentiated for five days in vitro in basal media, and then processed for immunocytochemistry to determine the number of β-tubulin immunopositive neurons. Data were normalized to those obtained with either EGF or FGF+HS alone (100%). As shown in FIG. 3, PACAP significantly increased the number of neurons generated, indicating that PACAP enhances neurogenesis. Furthermore, neurogenesis was enhanced independently of PACAP's effect on survival, because an increase was observed even when PACAP addition was delayed until after five days in vitro (PACAP at 5 DIV in FIG. 3).

PACAP Stimulates Akt and STAT5 Phosphorylation in Cultured Neural Stem Cells.

To examine the possible mechanisms of PACAP action on neural stem cells, the effects of PACAP on Akt and STAT5 phosphorylation were investigated. Immunoblots were performed with anti-STAT5 (1:1000, Santa Cruz Biotechnology), anti-phospho-STAT5 (1:1000; Cell Signaling Technology), anti-Akt and anti-phospho-Akt (1:1000; Cell Signaling Technology). Western blot analysis (data not shown) demonstrated that PACAP induced a rapid increase (within 1 to 2 hours) in phosphorylation of Akt, which is believed to be associated with cell survival. PACAP also stimulated STAT5 phosphorylation, which was previously shown to be important in neural stem cell neurogenesis. The effects of PACAP on Akt and STAT5 phosphorylation may be critical in mediating actions on neural stem cell survival and neurogenesis.

In vivo effects of PACAP.

As noted above, examination of the expression of $PAC_1$-R in the adult brain revealed abundant expression in the forebrain subventricular zone (SVZ). To examine the actions of the peptide in vivo, CD-1 mice (6–7 weeks of age) were implanted with osmotic minipumps (Alzet 1007D) filled with either human PACAP (American Peptide Company, 165 µg/ml) or vehicle alone (0.9% saline containing 1 mg/ml mouse serum albumin). The cannulae were placed in the right lateral ventricle. Each animal was infused for 6 days and injected with BrdU every two hours for ten hours and killed 0.5 hours after the last injection. Brains were processed for immunohistochemistry as described previously (Shingo et al., 2001) and BrdU+cells were counted in serial sections of the SVZ.

Figure 4:
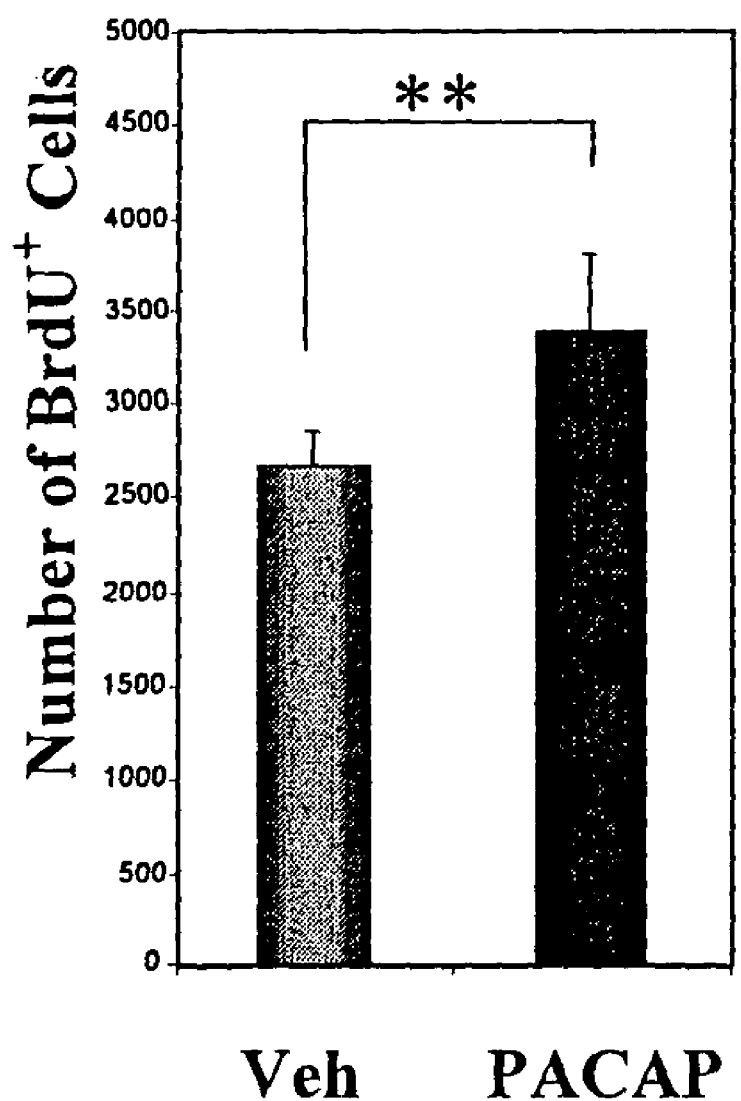
FIG. 4. PACAP infusion stimulated increased proliferation in the adult subventricular zone (SVZ) in vivo. PACAP was infused into the lateral ventricles for six days with an osmotic minipump, followed by a series of BrdU injections. Brains were processed for immunocytochemistry. PACAP increased proliferation in the adult SVZ. (** $p<0.05$, n=4).

As shown in FIG. 4, the number of BrdU incorporating cells was significantly increased in animals receiving PACAP infusions relative to control vehicle infused animals. Thus, PACAP increased proliferation in the adult forebrain SVZ.

Accordingly, the data discussed above demonstrate multiple, novel roles for PACAP in the regulation of both embryonic and adult neural stem cell populations and demonstrate the utility of PACAP for the treatment of neurodegenerative disease, brain injury, and CNS dysfunction.

Although the present invention has been described in detail with reference to examples above, it is understood that various modifications can be made without departing from the spirit of the invention, and would be readily known to the skilled artisan.

We claim:

1. A method for increasing neural stem cell and/or neural stem cell progeny number comprising: adding pituitary adenylate cyclase-activating polypeptide (PACAP) to multipotent neural stem cells in an amount effective to increase neural stem cell and/or neural stem cell progeny number, said method further comprising adding prolactin.

2. The method of claim 1, wherein the number of neural stem cells and/or neural stem cell progeny is increased by enhancing proliferation.

3. The method of claim 1, wherein the number of neural stem cells and/or neural stem cell progeny is increased by enhancing survival.

4. The method of claim 1, wherein the number of neural stem cells and/or neural stem cell progeny is increased by increasing secondary neural stem cells obtained from a primary neural stem cell.

5. The method of claim 1, wherein the neural stem cells are located in a subject.

6. The method of claim 5, wherein PACAP is added parenterally.

7. The method of claim 5, wherein the subject is a mammal.

8. The method of claim 7, wherein the subject is an adult.

9. The method of claim 7, wherein the subject is a human.

10. The method of claim 5, wherein the subject is suffering from a neurodegenerative disease or brain injury.

11. The method of claim 10, wherein the neurodegenerative disease is Alzheimer's Disease, Parkinson's Disease, or Huntington's Disease.

12. The method of claim 5, wherein the subject is suffering from a stroke.

13. The method of claim 5, wherein the increase in neural stem cell number occurs in the subventricular zone of the subject.

14. The method of claim 1, wherein the PACAP is PACAP38.

15. The method of claim 1, wherein the PACAP is PACAP27.

16. The method of claim 1, wherein the prolactin is added concurrently with PACAP.

17. The method of claim 1, wherein the prolactin is added sequentially with PACAP.

18. The method of claim 17 wherein the prolactin is added prior to the addition of PACAP.

19. The method of claim 17 wherein the prolactin is added after the addition of PACAP.

20. A method of increasing the number of neural stem cells and/or neurospheres in a culture comprising adding pituitary adenylate cyclase-activating polypeptide (PACAP) to a neural stem cell culture to increase the number of neural stem cells and/or neurospheres generated from the neural stem cell culture, said method further comprising adding prolactin.

21. The method of claim 20, wherein the neural stem cell culture is a primary culture.

22. The method of claim 20, wherein the neural stem cell culture is a clonal density culture.

23. The method of claim 20, further comprising adding a growth factor to the culture.

24. The method of claim 20, wherein the PACAP is PACAP38.

25. The method of claim 20, wherein the PACAP is PACAP27.

26. The method of claim 23, wherein the growth factor is fibroblast growth factor-2(FGF-2).

27. The method of claim 26, further comprising adding heparan sulfate.

28. The method of claim 23, wherein the growth factor is epidermal growth factor.

29. The method of claim 28, wherein the EGF is EGF51N or EGF51Q.

30. A method of enhancing differentiation of neural stem cells in a subject comprising administering pituitary adenylate cyclase-activating polypeptide (PACAP) to the subject in an amount sufficient to enhance differentiation of neural stem cells, said method further comprising administering prolactin.

31. The method of claim 30, wherein differentiation of neural stem cells into neurons is enhanced.

32. The method of claim 30, wherein the PACAP is PACAP38.

33. The method of claim 30, wherein the PACAP is PACAP27.

34. The method of claim 30, wherein the subject is a mammal.

35. The method of claim 34, wherein the subject is an adult.

36. The method of claim 34, wherein the subject is a human.

37. The method claim 30, wherein the prolactin is administered to the subject prior to the administration of PACAP.

38. The method claim 30, wherein the prolactin is administered to the subject after the administration of PACAP.

39. The method of claim 30, wherein the subject is suffering from a neurodegenerative disease or brain injury.

40. The method of claim 39, wherein the neurodegenerative disease is Alzheimer's Disease, Parkinson's Disease, or Huntington's Disease.

41. The method of claim 30, wherein the subject is suffering from a stroke.

42. The method of claim 30, wherein the differentiation of neural stem cells occurs in the subventricular zone.

* * * * *